United States Patent
Tennican

(10) Patent No.: US 10,322,241 B2
(45) Date of Patent: Jun. 18, 2019

(54) INJECTION SYSTEMS WITH STORAGE COMPARTMENTS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 0 days.

(21) Appl. No.: 15/561,957

(22) PCT Filed: Mar. 24, 2016

(86) PCT No.: PCT/US2016/024089
§ 371 (c)(1),
(2) Date: Sep. 26, 2017

(87) PCT Pub. No.: WO2016/160530
PCT Pub. Date: Oct. 6, 2016

(65) Prior Publication Data
US 2018/0110918 A1    Apr. 26, 2018

Related U.S. Application Data

(60) Provisional application No. 62/139,582, filed on Mar. 27, 2015.

(51) Int. Cl.
*A61M 5/31* (2006.01)
*B65D 83/10* (2006.01)
(Continued)

(52) U.S. Cl.
CPC ............ *A61M 5/31511* (2013.01); *A61J 1/03* (2013.01); *A61M 5/002* (2013.01); *A61M 5/008* (2013.01);
(Continued)

(58) Field of Classification Search
CPC .......... A61J 1/03; A61M 5/001; A61M 5/002; A61M 5/008; A61M 5/19; A61M 5/31501;
(Continued)

(56) References Cited

U.S. PATENT DOCUMENTS

| 776,402 A | 11/1904 | Johnson |
| 1,024,674 A | 4/1912 | Briggs |

(Continued)

FOREIGN PATENT DOCUMENTS

| DE | 1922884 | 11/1969 |
| WO | WO2013130891 A1 | 9/2013 |
| WO | WO2014144416 | 9/2014 |

OTHER PUBLICATIONS

Barnes, et al., "A Woman's Guide to Diabetes: A Path to Wellness", American Diabetes Association, Nov. 21, 2014, 4 pages.
(Continued)

*Primary Examiner* — Bryon P Gehman
(74) *Attorney, Agent, or Firm* — Lee & Hayes, P.C.

(57) ABSTRACT

Injection systems with storage compartments to house various materials are described. The storage compartments facilitate provision of medical care in space- and time-efficient manners and are particularly useful in providing care in non-medical facilities.

19 Claims, 7 Drawing Sheets

(51) Int. Cl.
*A61M 5/315* (2006.01)
*A61M 5/00* (2006.01)
*A61J 1/03* (2006.01)
*A61M 5/178* (2006.01)
*A61M 5/50* (2006.01)

(52) U.S. Cl.
CPC ......... *A61M 5/31501* (2013.01); *A61M 5/178* (2013.01); *A61M 2005/5033* (2013.01); *A61M 2209/06* (2013.01)

(58) Field of Classification Search
CPC ............ A61M 5/31511; A61M 5/3202; A61M 2005/5033; A61M 2209/06; A61M 5/31; A61M 5/32; B65D 83/00; B65D 83/10
USPC ................ 206/364, 365, 571, 738, 755, 366
See application file for complete search history.

(56) References Cited

U.S. PATENT DOCUMENTS

| | | | |
|---|---|---|---|
| 4,243,035 A | | 1/1981 | Barrett |
| 4,429,793 A | * | 2/1984 | Ehmann ................ A61M 5/003 206/366 |
| 4,657,138 A | * | 4/1987 | Watson .................. A61B 50/31 206/366 |
| 5,163,557 A | * | 11/1992 | Sokolowski ........... A61B 50/33 206/571 |
| 5,533,625 A | | 7/1996 | Mikkelsen |
| 6,398,027 B1 | | 6/2002 | Ryu |
| 7,753,203 B2 | | 7/2010 | Lampropoulos et al. |
| 9,889,248 B2 | * | 2/2018 | Head ..................... A61M 5/002 |
| 2004/0069667 A1 | | 4/2004 | Tomellini et al. |
| 2005/0203464 A1 | | 9/2005 | Haider et al. |
| 2006/0079834 A1 | | 4/2006 | Tennican et al. |
| 2007/0167917 A1 | | 7/2007 | Lee |
| 2008/0086091 A1 | | 4/2008 | Anderson et al. |
| 2010/0051491 A1 | | 3/2010 | Lampropoulos et al. |
| 2010/0059560 A1 | * | 3/2010 | Lanum .................. A61B 50/31 206/571 |
| 2011/0201867 A1 | | 8/2011 | Wagner |
| 2012/0109073 A1 | | 5/2012 | Anderson et al. |
| 2013/0178804 A1 | | 7/2013 | Tennican |
| 2015/0060462 A1 | | 3/2015 | Colbert et al. |
| 2015/0164743 A1 | * | 6/2015 | Janson ..................... A61J 1/05 206/571 |
| 2016/0030671 A1 | * | 2/2016 | Tennican ................ A61M 5/19 604/191 |
| 2018/0318515 A1 | | 11/2018 | Tennican |

OTHER PUBLICATIONS

PCT Invitation to Pay Additional Fees dated May 31, 2016 for PCT Application No. PCT/US16/24095, 2 pages.
PCT Invitation to Pay Additional Fees dated Jun. 8, 2016 for PCT application No. PCT/US16/24089, 2 pages.
PCT Search Report and Written Opinion dated Oct. 20, 2016 for PCT Application No. PCT/US16/24089, 14 pages.
PCT Search Report and Written Opinion dated Aug. 26, 2016 for PCT Application No. PCT/US16/24095, 14 pages.
Extended European Search Report dated Jul. 9, 2018 for European patent application No. 16773809.5, 8 pages.
The Extended European Search Report dated Sep. 20, 2018, for European Application No. 16773810.3, 8 pages.
Final Office dated Jan. 9, 2019 for U.S. Appl. No. 15/561,949 "Injection Systems With Storage Compartments" Tennican, 12 pages.
Office Action for U.S. Appl. No. 15/561,949, dated on Sep. 18, 2018, Patrick O. Tennican, "Injection Systems With Storage Compartments", 15 pages.
Office Action for U.S. Appl. No. 15/561,949, dated Apr. 24, 2019, Tennican, "Injection Systems With Storage Compartments", 12 pages.

* cited by examiner

INJECTION SYSTEMS WITH STORAGE COMPARTMENTS

CROSS REFERENCE TO RELATED APPLICATIONS

This application is the national stage of International Application No. PCT/US16/24089 filed 24 Mar. 2016, which claims priority to, and the benefit of, U.S. Provisional Application No. 62/139,582, filed Mar. 27, 2015, the entire contents of which are incorporated by reference herein.

FIELD OF THE DISCLOSURE

The disclosure provides for injection systems with storage compartments to house various materials. The storage compartments facilitate provision of medical care in space and time-efficient manners and are particularly useful in providing care in non-medical facilities.

BACKGROUND OF THE DISCLOSURE

Time is critical in responding to a number of medical conditions. For example, a person suffering from anaphylactic shock due to an allergy may need medication delivered shortly after a reaction begins. Often, however, the person may be in a location far from a medical facility. Even within medical facilities, reducing the time necessary to treat a subject can enhance treatment outcomes.

SUMMARY OF THE DISCLOSURE

Disclosed herein are injection systems with storage compartments. The systems provide compact medical care that can be carried with a person in the event medical care becomes necessary outside of a medical facility. The systems can also be used within medical facilities to streamline access to medications and supplies that are often used together.

An embodiment disclosed herein includes one or more syringes housed together in a box or pouch. The housing may include one or more storage compartments. Plungers within these syringes may additionally include a storage compartment. Each syringe of the one or more syringes housed together in a box or pouch can be associated with a hinge system that facilitates handling and use of the syringe.

Each of the embodiments disclosed herein facilitates provision of medical care in non-medical and medical facilities.

BRIEF DESCRIPTION OF THE FIGURES

FIGS. 2A-2D depict inclusion of various medications (FIG. 2A (capsule); FIG. 2B (tablet)) or medical supplies (FIG. 2C (folded antiseptic wipe); FIG. 2D (sponge)) within the storage compartments.

DETAILED DESCRIPTION

Figure 1:
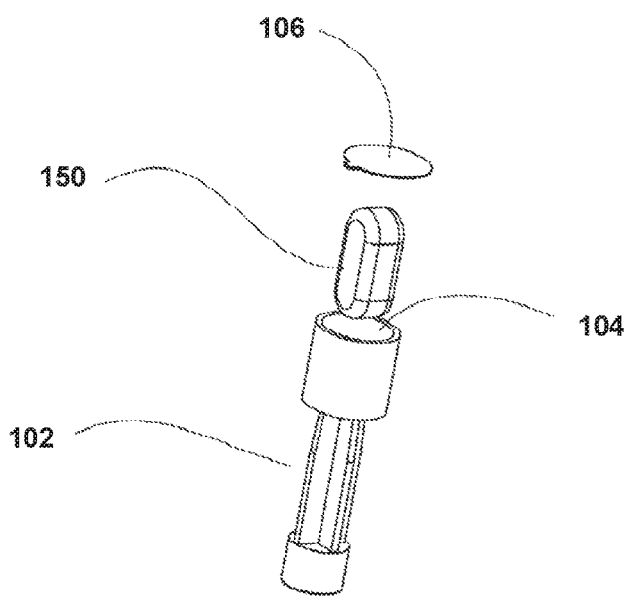
FIG. 1 depicts a syringe plunger with a storage compartment.

Time may be critical for responding to certain medical conditions. For example, a person or animal suffering from anaphylactic shock may need medication delivered shortly after a reaction begins. If the necessary medications and medical supplies are not pre-assembled into an easy-to-access and easy-to-use configuration, valuable time may be lost. Thus, combining multiple medications, multiple delivery mechanisms of the medications (e.g., intravenous, oral, sublingual, and intracardiac), the means to administer the medications, and/or applicators having an antiseptic composition into a single easy to use injection system provides significant benefits.

Disclosed herein are injection systems that facilitate administration of medical treatments by providing injection systems with storage compartments. The injection systems with storage compartments allow various medications and medical supplies to be housed together in space- and use-efficient manners. The space-efficient designs allow more medications and medical supplies to be carried on individuals outside of a medical care facility. The use-efficient designs promote ease of administration, shortening the time required to assemble and safely administer various medications.

The injection systems can be provided to end users without medications pre-provided or pre-loaded. In these embodiments, an end user can select and load medications and supplies into the injection systems. In further embodiments, the injection systems can come with medical supplies, but not medications pre-loaded. Medical supplies include any object that facilitates administration of a medication, for example, cotton, gauze, bandages, tubing, needles, saline, antiseptic wipes, stents, funnels, tips, etc. In particular embodiments, medical supplies can be housed in the storage compartments. In further embodiments, the injection systems can come pre-loaded with medications but not medical supplies. In still further embodiments, the injection systems can come pre-loaded with medications and medical supplies.

In use, the injection systems include a primary medication. A primary medication is one that is intended to treat a medical condition that an end user may experience or encounter. For example, if the end user is prone to severe allergic reactions or is likely to spend time with a person or animal prone to severe allergic reactions, the primary medication could be epinephrine. The primary medication can be housed in a storage compartment or can be pre-loaded into the medication chamber of a syringe.

In other particular embodiments, injection systems can include one or more of a supporting medication, a redundant dose, and/or a supplemental medication. The supporting medication, redundant dose, and/or supplemental medication can be housed within a storage compartment and/or can be pre-loaded into a medication chamber not housing the primary medication.

A supporting medication is a medication that is not intended to treat the medical condition likely to be experienced or encountered, per se, but nonetheless, provides a beneficial effect to support the main treatment objective of the primary medication. For example, if the injection system is configured to treat allergic reactions, the primary medication could be epinephrine and the supporting medication could be an antiseptic, an antibiotic, an anti-anxiety medication, or a pain management medication.

A redundant dose is an additional dose of the primary medication. Redundant doses can be provided in the event that the primary dose is unexpectedly not high enough to address the medical condition at issue, or in the event that there is a system failure resulting in incomplete administration of the primary medication dose. Redundant doses can also be provided for treatment regimens where repeated dosing over time is warranted.

A supplemental medication is a second, different medication that is intended to treat the same medical condition that the primary medication is intended to treat. For example, for an allergic reaction, the primary medication can include epinephrine and the supplemental medication can be an antihistamine or a steroid. In particular embodiments, the supplemental medication is intended to treat the same medical condition as the primary medication but through a different mechanism of action.

Embodiments of injection systems disclosed herein include plungers for syringes, syringes, and portable kits. Each of these types of injection systems is described more fully in reference to the various figures. The same reference number is used throughout the figures to depict the same or similar feature(s) of the illustrative devices and systems.

FIG. 1 depicts a syringe plunger 102 with a storage compartment 104. A capsule 150 for oral administration is depicted, although as indicated elsewhere, various forms of medications and medical supplies may be housed within the storage compartment 104. The storage compartment 104 can be within the syringe itself 110 or can be independent of the syringe, for example, in a housing 108, provided elsewhere within the injection system.

In this depicted embodiment, the storage compartment includes a lid 106. The lid 106 can be any mechanism capable of substantially maintaining the housed medication and/or medical supply within the storage compartment 104 so that it is ready for use when needed. Exemplary lid mechanisms include friction-fit caps, snap-caps, screw caps, films, foils, cloths and covers. In some embodiments, a seal may be used in addition to a lid. In such embodiments, the seal may be in place to maintain sterility of the medication and/or the medical supply. Exemplary seals include films, foils, covers, and the like.

Figures 2A, 2B:
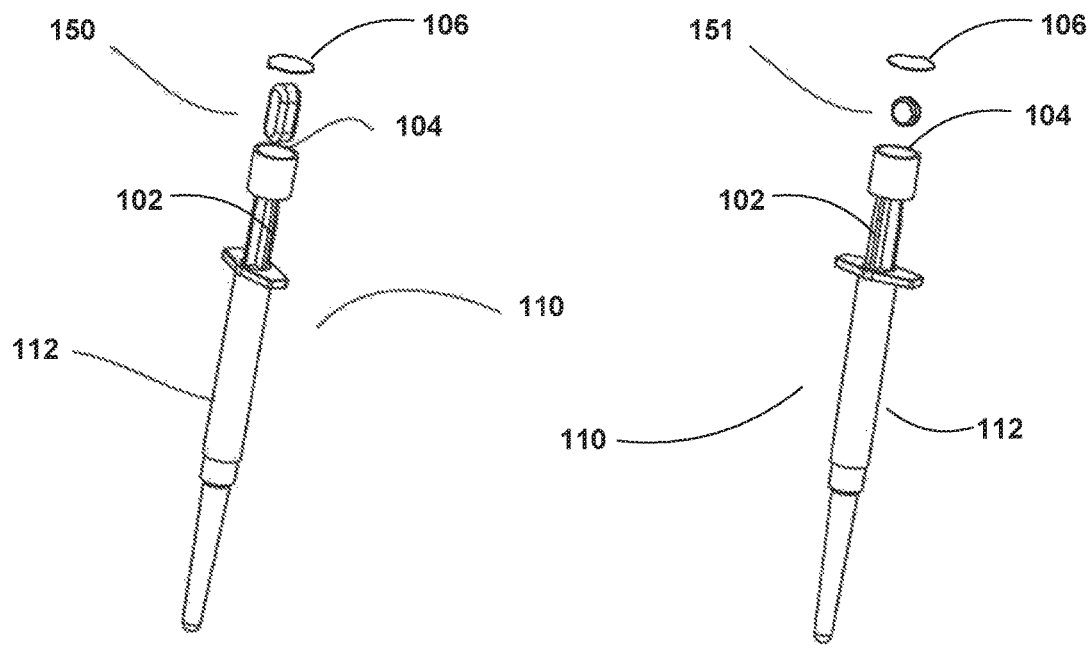
FIGS. 2A-2D depict plungers with a storage compartments associated with syringes.
Figure 2C:
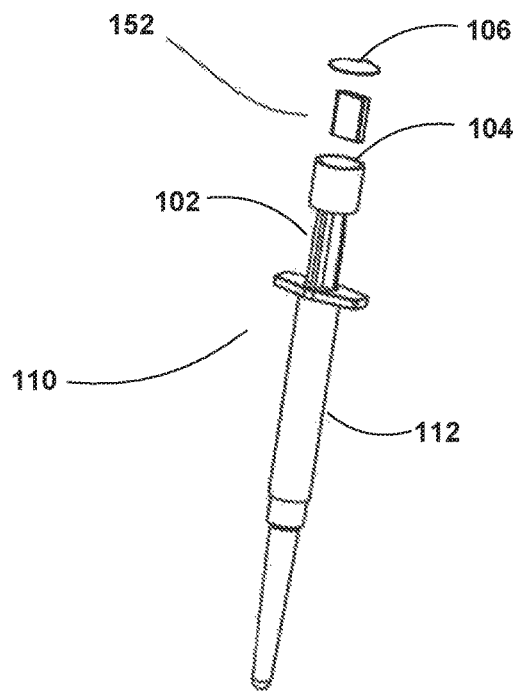
Figure 2D:
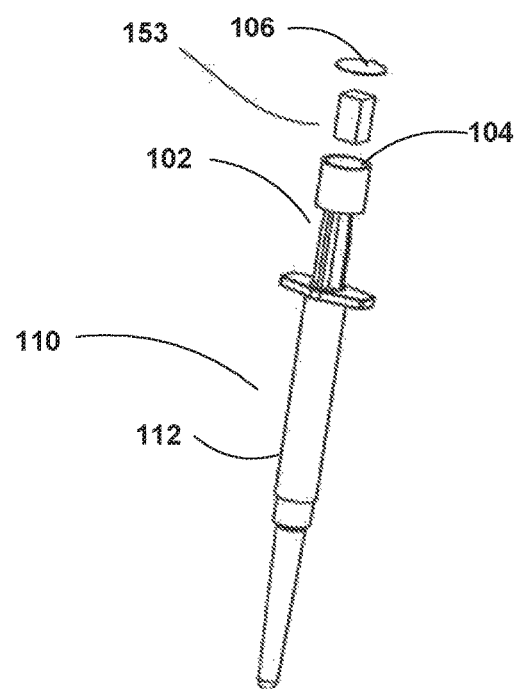

FIGS. 2A-2D depict plungers 102 with storage compartments 104 associated with a medication chamber 112 to form a syringe 110. In these FIGs., the depicted medication is a capsule 150 (FIG. 2A) or a tablet 151 (FIG. 2B) and/or the medical supply is an antiseptic wipe 152 (FIG. 2C) or a sponge 153 (FIG. 2D).

Figure 3:
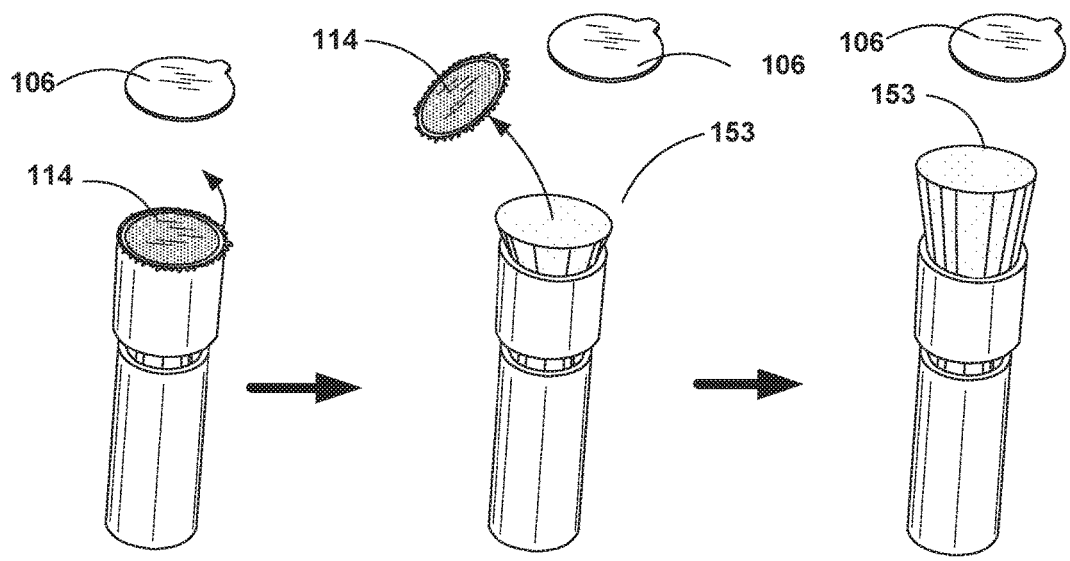
FIG. 3 depicts a compressed sponge stored in a storage compartment.

As can be seen in FIG. 3, medical supplies such as a sponge 153 can be stored in a compressed state, optionally with a seal 114 to maintain sterility, and optionally under a lid 106. In embodiments where the medical supply is sealed into the storage compartment, the seal may be removed and the medical supply, such as a sponge, may expand and extend beyond the walls of the storage compartment, as illustrated in FIG. 3. In some embodiments, the sponge can contain an antiseptic solution or antiseptic gel.

Figure 4:
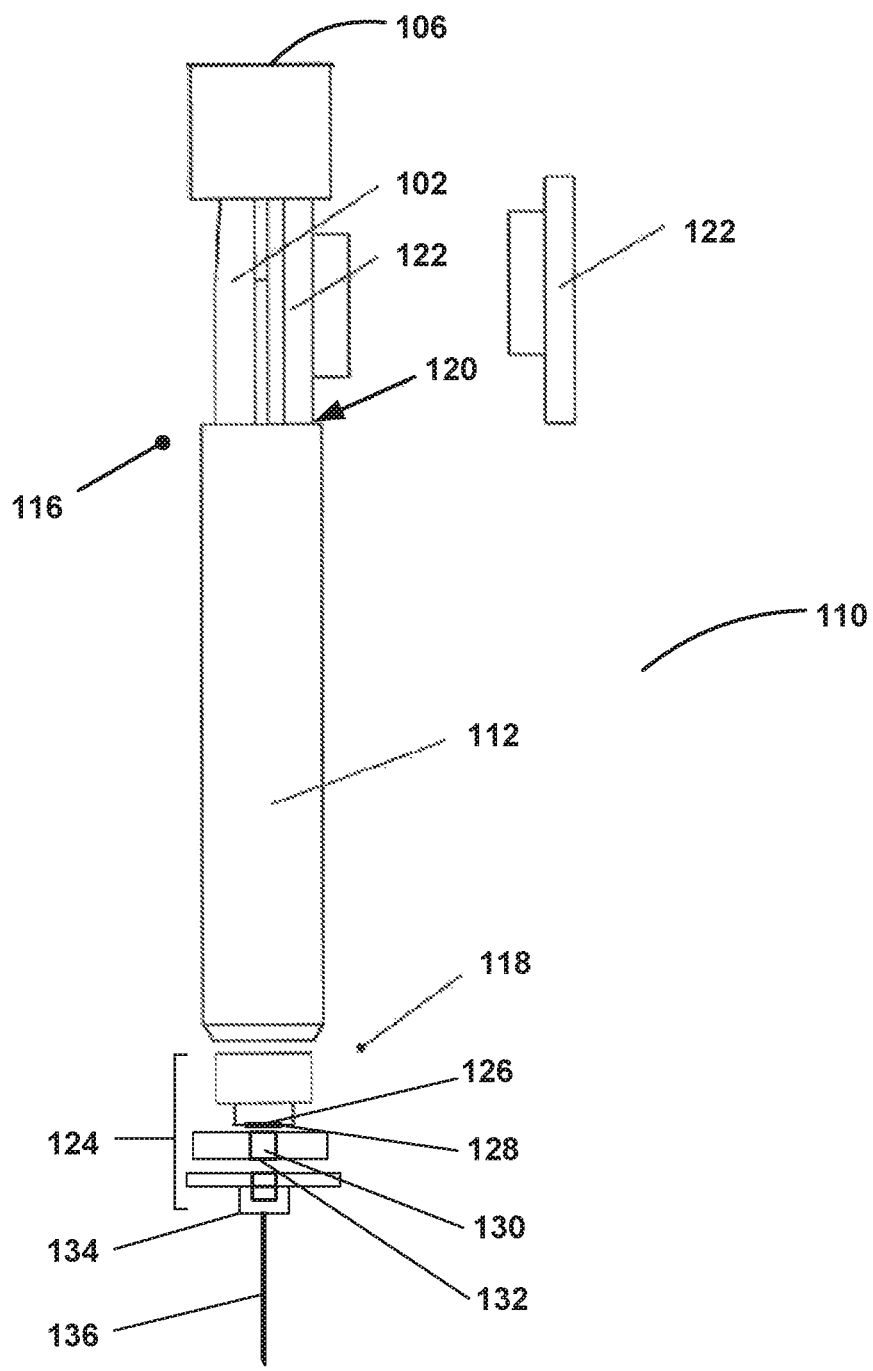
FIG. 4 shows a side view of an injection device including a plunger with a storage compartment and a plunger safety lock.

As shown in FIG. 4, a syringe 110 has one or more medication chambers 112 having a proximal end 116, a distal end 118, and a chamber cavity 120 that may have contents pre-loaded therein. The chambers 112 may also be associated with a plunger 102 to expel the contents of the chamber 112 when force is applied to the end of the plunger 102. The chambers 112 may be generally cylindrical and may be formed separately. In some embodiments, the syringes 110 may be associated with each other through a housing, clip, or other mechanism. Alternatively, multiple chambers 112 may be formed from a single piece of material (e.g., plastic, glass, steel, etc.). The chamber cavities 112 may include a lid 106.

In some embodiments, the syringe 110 may include a plunger safety lock 122 which prevents each plunger 102 from being depressed, thus preventing premature expulsion of any contents of the chamber(s) 112. According to an embodiment, the plunger safety lock 122 may be removed by, for example, snap removal.

Embodiments disclosed herein can be used with any plunger, syringe, or syringe system. Exemplary plungers, syringes, and syringe systems include Luer-lock syringes, Air-Tite syringes, syringes made available by Becton Dickinson, AllegroMedical, Cole-Palmer, and Catalent, EPI-PEN (Mylan, Canonsburg, Pa.), and Allerject (Sanofi, Laval, Quebec).

According to an embodiment, an outlet body 124 may be connected to the distal end 116 of a chamber 112 of the syringe 110. According to certain embodiments, each opening 126 may be surrounded by opening seal 128 to help ensure a tight connection between the opening 126 and outlet 130. In other embodiments, the outlet 130 may be surrounded by an outlet seal 132 to ensure a tight connection between the opening 126 and outlet 130. The outlet 130 may be a hole that is connected to a hollow needle such as a hypodermic needle 136. In some implementations, the outlet 130 may include a connector 134 such as a tapered connector or a locking connector. The connector 134 may form a fluid-tight seal between the chamber 112 and object (such as, for example, a hypodermic needle or tube) coupled to the other end of the connector 134. Examples of such connectors 134 include a Luer tapered connector, a Luer lock connector, and a Luer slip connector. The other end of the connector 134 may be coupled to a needle with a corresponding (e.g., female) connector. Alternatively, the other end of the connector 134 may be coupled to a catheter or stent.

Figure 5:
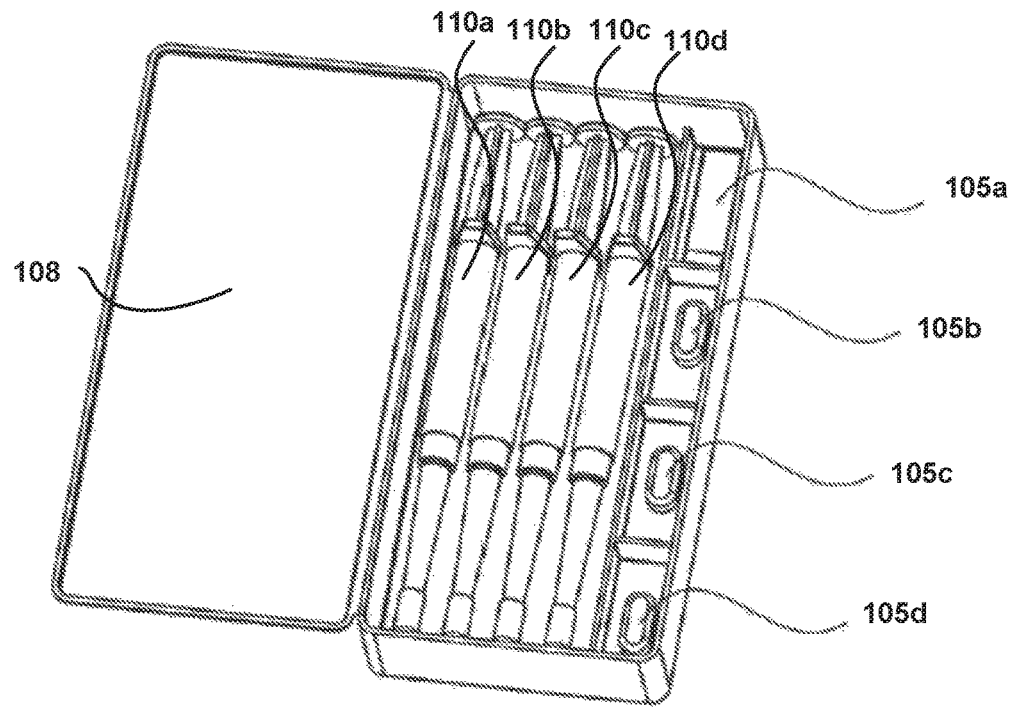
FIG. 5 depicts a group of syringes housed together in a box or pouch wherein the box or pouch provides for storage. The syringes are in a storage position.

FIG. 5 depicts a group of syringes 110a-110d (collectively and individually referred to as 110) housed together in a housing 108, such as a box or pouch, wherein the housing provides for storage compartments in numerous potential configurations. The injection system 100 is shown with four syringes 110, but the injection system 100 may have a greater or lesser number of syringes 110.

In some embodiments, the syringes 110 may have syringe caps 138 which are used when the syringe is not in use. The syringe caps 138 are fitted to the distal end 118 of a chamber 112 of the syringe 110, and can facilitate storage and selection of the syringe 110. In some embodiments, the syringe caps 138 may connect to, or be a part of, a hinge mechanism 140, housing 108, or a rod 148. The syringe caps can hold the syringes by any suitable method, such as, for example, pressure fit, screw fit, and the like. In various embodiments, the syringe caps can be friction-fit caps, snap-caps, screw caps, or any other suitable caps.

The injection system 100 may be prepared and presented to a user with contents already inside of one or more of the chambers 112 of the one or more syringes 110.

The contents of the chambers 112 of each syringe 110 may be solids, gases, or fluids. The contents may include single compounds or compositions of multiple compounds. In some embodiments, the contents may be pre-mixed or otherwise prepared for administration before being inserted into the chamber 112. In other embodiments, the contents may be separated by a film or other membrane that is broken when force is applied to the plunger 102. The contents may be medication or other non-medicinal contents such as, for example, saline or water.

Each of the multiple syringes 110 may contain the same or different contents. In some implementations, two or more syringes 110 (such as, for example, 110a and 110b) may contain the same contents while other syringes 110 contain one or more different contents. Providing the same contents (e.g., redundant doses) in two or more syringes 110 provides redundancy and allows the user to administer a second dose if administration of the contents of one syringes 110 fails. For example, this can provide a backup functionality in case there is a failure either with the syringe 110 or with the use of the syringe 110. In other embodiments, this can be used in association with treatment regimens where repeated dosing over time is warranted.

Separating the same contents into multiple different syringes 110 may also allow for simple adjustment of dosage. That is to say, it may be easier for the user, and lead to a more precisely administered dose, to fully dispense the contents of a syringe 110 and then, if necessary, use the entire contents of a second syringe 110 rather than partially dispensing the contents of a syringe 110 followed by dispensing the remaining contents of the syringe 110. Because the injection system may have any number of syringes 110, various volumes or dosages may be readily achieved. In various embodiments, dosage can be customized to a particular end-user. For example, dosage can be determined based on body weight, drug clearance rate, age (e.g., infant, pediatric, adult, etc.), and the like.

When one or more of the syringes 110 is pre-loaded there may also be one or more other syringes 110 that are not pre-loaded. Empty syringes 110, if present, may remain unused (e.g., the injection system 100 has four syringes 110a-110d but only three syringes 110a-110c are needed for a particular application) or the empty syringes 110d, for example, may be filled by the user at, or shortly before, the time of use.

In one aspect, the injection system 100 may have the syringes 110 pre-loaded with medications intended to be used together to treat a specific medical need. For example, treatment of a strong allergic reaction such as anaphylaxis may be addressed by injection of epinephrine (adrenaline, a primary medication), an antihistamine (a supplemental medication), a steroid (a supplemental medication), an anti-anxiety medication (a supporting medication), and/or a pain management medication (a supporting medication). The antihistamine may be diphenhydramine or a similar antihis-tamine. The steroid may be a corticosteroid such as cortisone, prednisone, methylprednisolone (MEDROL® (Pharmacia & Upjohn Company LLC, Peapack, N.J.)), and dexamethasone (DECADRON® (Pragma Pharmaceuticals LLC, Locust Valley, N.Y.)).

In one example, a first syringe 110a of the injection system 100 can contain epinephrine, a second syringe 110b of the injection system 100 can contain an antihistamine, a third syringe 110c of the injection system 100 can contain a pain management medication, and a fourth syringe 110d of the injection system 100 may be pre-loaded with another dose of epinephrine (a redundant dose). In this implementation, each of the medications in the syringes 110 of the injection system 100 is related to treatment of the same medical condition namely allergic reaction. Equipping one injection system 100 with multiple medications can provide a range of anti-allergy therapy, i.e., for anaphylaxis, from quick action/short duration, (epinephrine), intermediate action/intermediate duration (antihistamine) to longest onset action/greatest duration of activity (corticosteroid). This configuration places different medications suitable for treating different aspect of a severe allergic reaction together in a single device. Thus, adrenaline may be administered immediately after the reaction begins, the antihistamine may be administered after the subject initially stabilizes, and the corticosteroid may be administered if there is a prolonged delay receiving professional medical care.

Contents of the syringes 110 may be co-administered or may be administered sequentially to a subject. This sequential administration may be in rapid succession, or may be delayed and subsequent medications may be administered based on response of the subject to the previous administered medication or medications. Contents of the chambers 112 may be administered intramuscularly, subcutaneously, or intravenously with a needle. Contents of the chambers 112 may be administered through an injection or infusion. Injection allows the contents, such as medication, of the chambers 112 to be quickly mobilized to the bloodstream. Contents of the chambers 112 may be administered intravenously with a coupling to a stent. Contents may also be administered intranasally with an appropriate tip (not shown) coupled to the syringe.

Two or more of the chambers 112 may have the same or different volumes. In some implementations, the volume of one or more chambers 112 may be about 1 mL, about 2 mL, about 5 mL, about 10 mL, about 20 mL, about 30 mL, about 40 mL, about 50 mL, about 60 mL, about 70 mL, about 80 mL, about 90 mL, about 100 mL, about 110 mL, about 120 mL, about 130 mL, or about 140 mL. In other implementations, the volume of one or more chambers 112 may be at least 1 mL, at least 2 mL, at least 5 mL, at least 10 mL, at least 20 mL, at least 30 mL, at least 40 mL, at least 50 mL, at least 60 mL, at least 70 mL, at least 80 mL, at least 90 mL, at least 100 mL, at least 110 mL, at least 120 mL, at least 130 mL, or at least 140 mL. In further implementations, the volume of one or more chambers 112 may be no more than 1 mL, no more than 2 mL, no more than 5 mL, no more than 10 mL, no more than 20 mL, no more than 30 mL, no more than 40 mL, no more than 50 mL, no more than 60 mL, no more than 70 mL, no more than 80 mL, no more than 90 mL, no more than 100 mL, no more than 110 mL, no more than 120 mL, no more than 130 mL, or no more than 140 mL. The volume may be selected based on known volumes of medication suitable for treating a particular medical condition.

Figure 6:
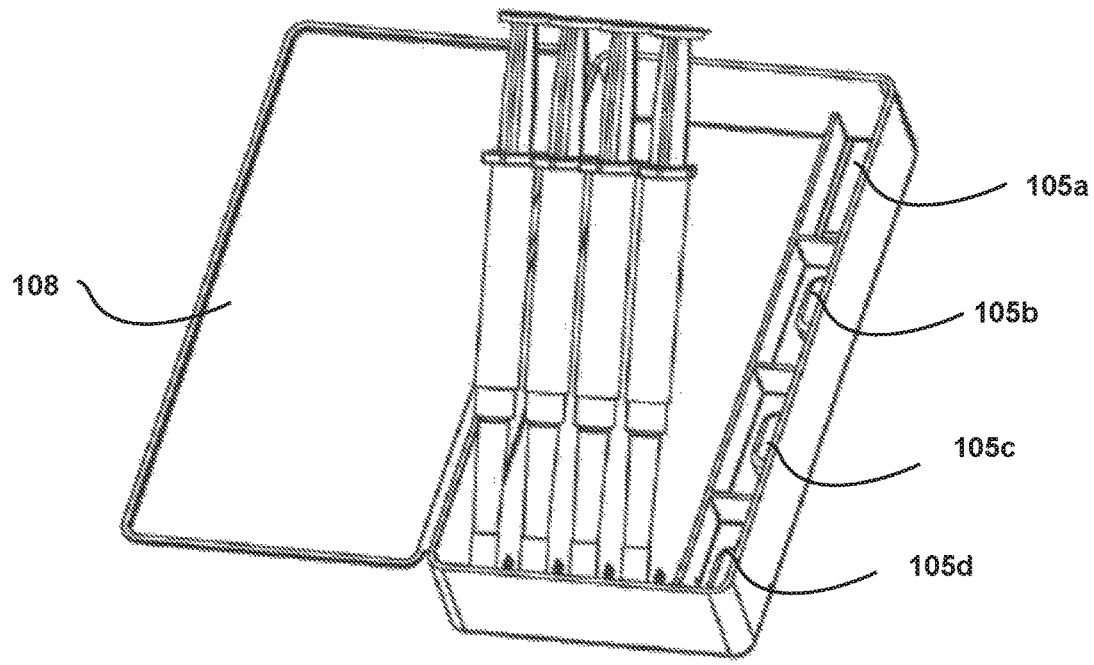
FIG. 6 depicts a group of syringes housed together in a box or pouch, with all syringes in an in-use position.

In the depicted embodiments of FIGS. 5 and 6, four storage compartments 105a-105d (collectively and individually referred to as 105) are provided. Each compartment 105 can house the same or different medications or medical supplies. One or more of the storage compartments may also include a lid or other cover (not shown). For example, particular storage compartments 105 may be sealed with a seal 114 such as a film, foil, or cap.

The syringes 110 are depicted in a storage position. The storage position provides space-efficient housing for the syringes 110 when not in use. Generally, the storage position will include the syringes 110 arranged in a parallel fashion along the base of the housing 108, such as a box or pouch.

FIG. 6 depicts an embodiment, which is the same as, or similar to, the embodiment depicted in FIG. 5, with the syringes 110 depicted in an in-use position. An in-use position reflects a departure from a storage position where the departure renders the syringes 110 more readily-available to an end user.

Figure 7:
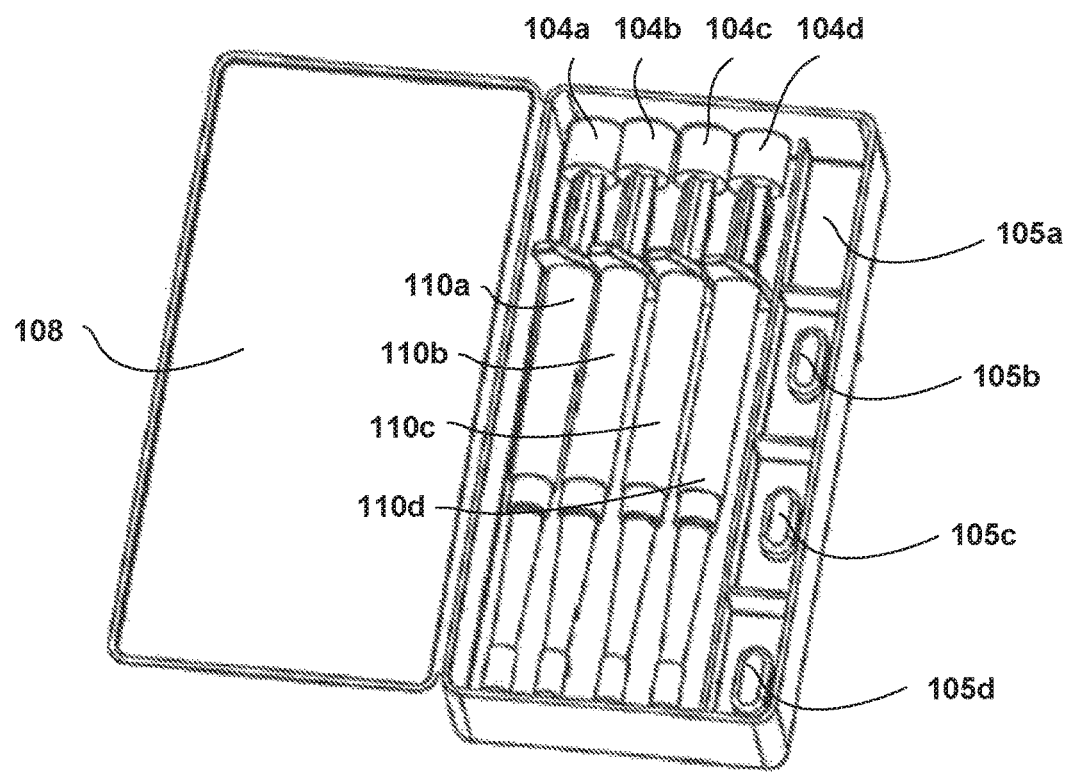
FIG. 7 depicts a group of syringes having plungers with storage compartments housed together in a box or pouch wherein the box or pouch provides for additional storage. The syringes are in a storage position.
Figure 8:
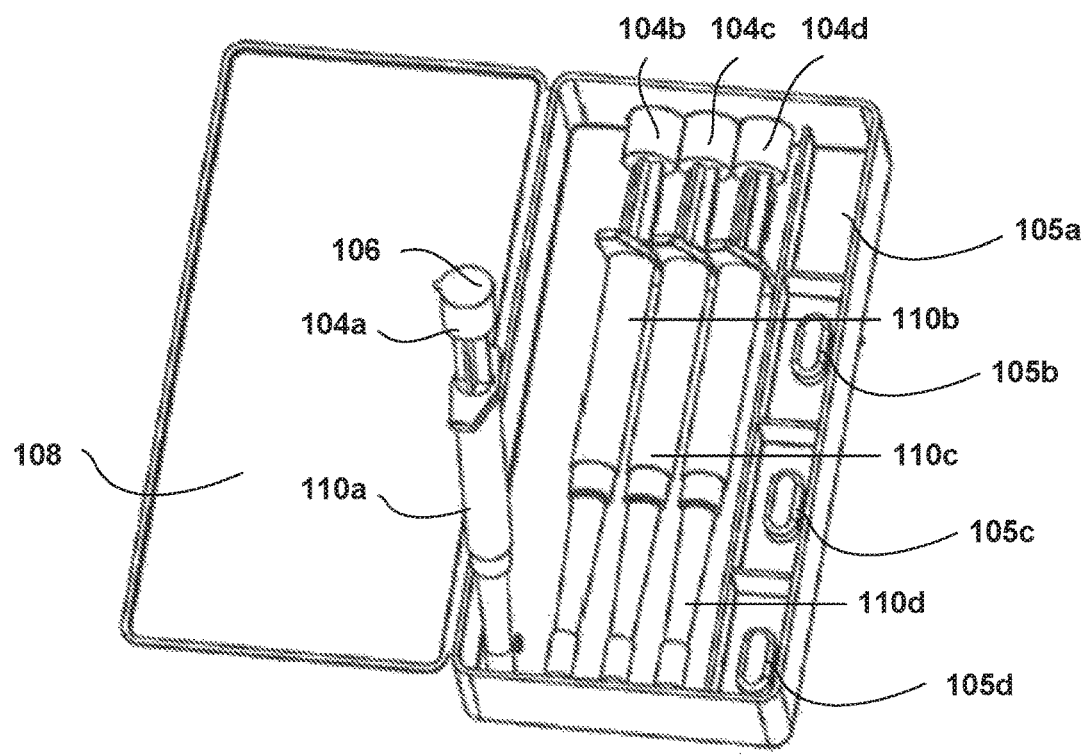
FIG. 8 depicts a group of syringes having plungers with storage compartments housed together in a box or pouch, with one syringe in an in-use position.

FIG. 7 depicts a group of syringes 110*a*-110*d* having plungers 102*a*-102*d* with storage compartments 104*a*-104*d* housed together in a box or pouch 108 wherein the box or pouch provides for additional storage in further storage compartments 105*a*-105*d*. In this illustrative embodiment, the syringes 110 are depicted in a storage position. FIG. 8 depicts an embodiment, which is the same as, or similar to the embodiment depicted in FIG. 7, with one syringe 110*a* in an in-use position.

Figure 9:
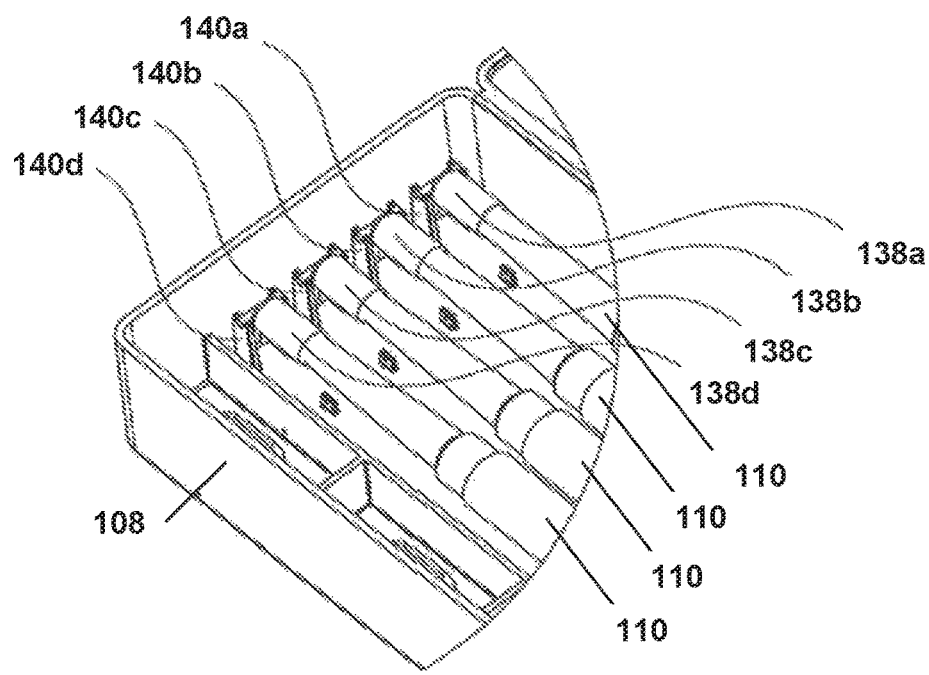
FIG. 9 depicts a close up view of hinge mechanisms associated with syringes in a box or pouch with the syringes in a storage position.
Figure 10:
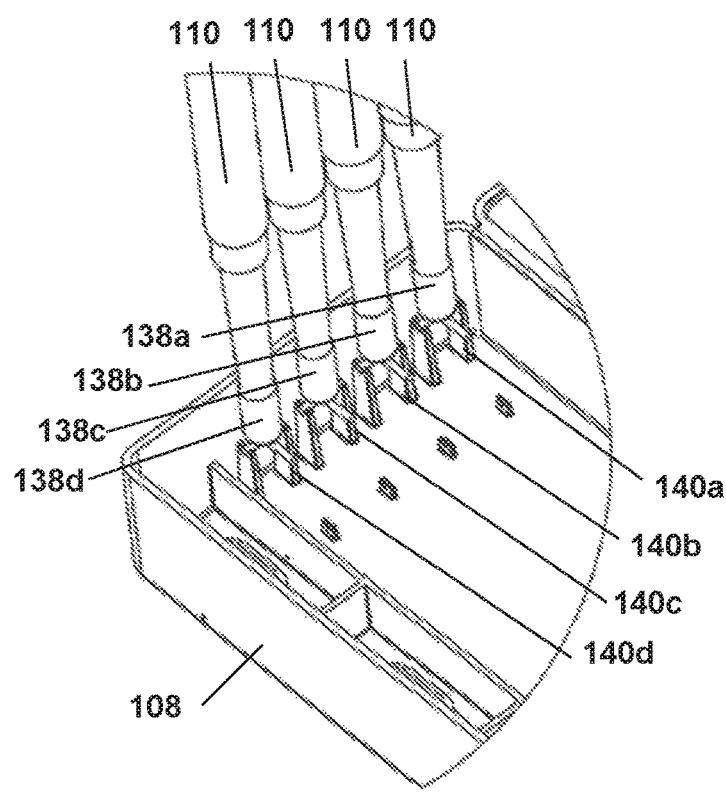
FIG. 10 depicts a close up view of hinge mechanisms associated with syringes in a box or pouch with the syringes in an in-use position.

FIG. 9 depicts a close-up view of individual hinge mechanisms 140*a*-140*d* (collectively and individually referred to as 140) associated with individual syringe caps 138*a*-138*d* (collectively and individually referred to as 138) in a housing 108 with the syringes 110 in a storage position. The hinge mechanisms 140 allow the syringes 110 to rotate longitudinally from a storage position to an in-use position. FIG. 10 depicts an embodiment, which is the same as, or similar to, the embodiment depicted in FIG. 9, with the syringes 110 in an in-use position.

Figure 11:
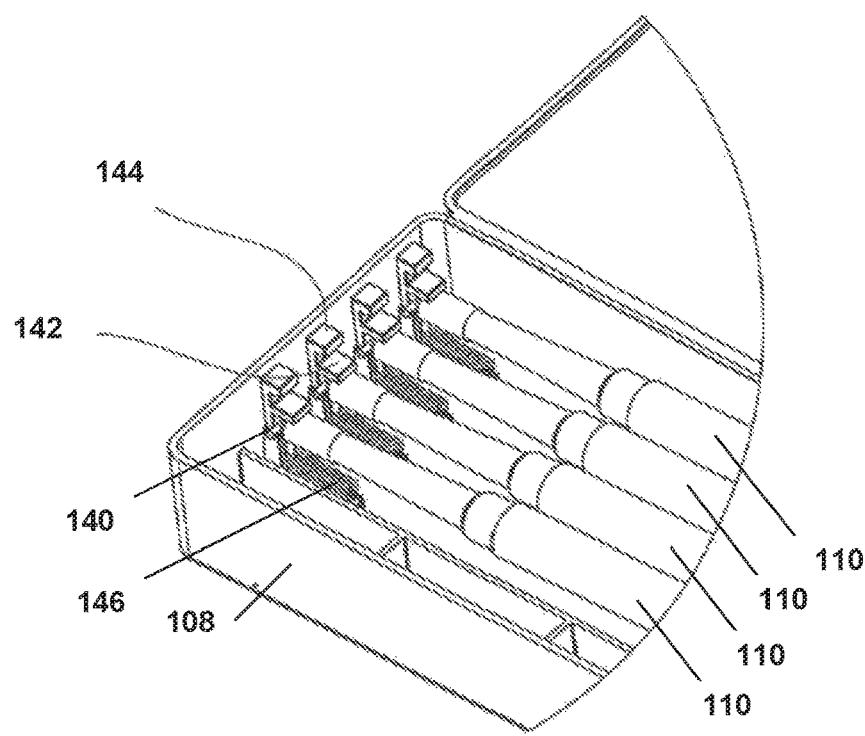
FIG. 11 depicts a close up view of hinge mechanisms associated with syringes in a box or pouch, the hinge mechanism providing a force to bias the syringes into an in-use position.

FIG. 11 depicts a close up view of an embodiment of hinge mechanisms 140 associated with syringes 110 in a housing 108, the hinge mechanisms 140 providing a force to bias the syringes into an in-use position. As can be seen, the syringes 110 are held in the storage position by a constraint 142. The constraint 142 can be removed, for example, by retracting the constraint directly or through a constraint removal piece 144. Following removal of the constraint 142, the biasing force (e.g., a spring) 146 biases the syringe 110 into an in-use position.

Figure 12:
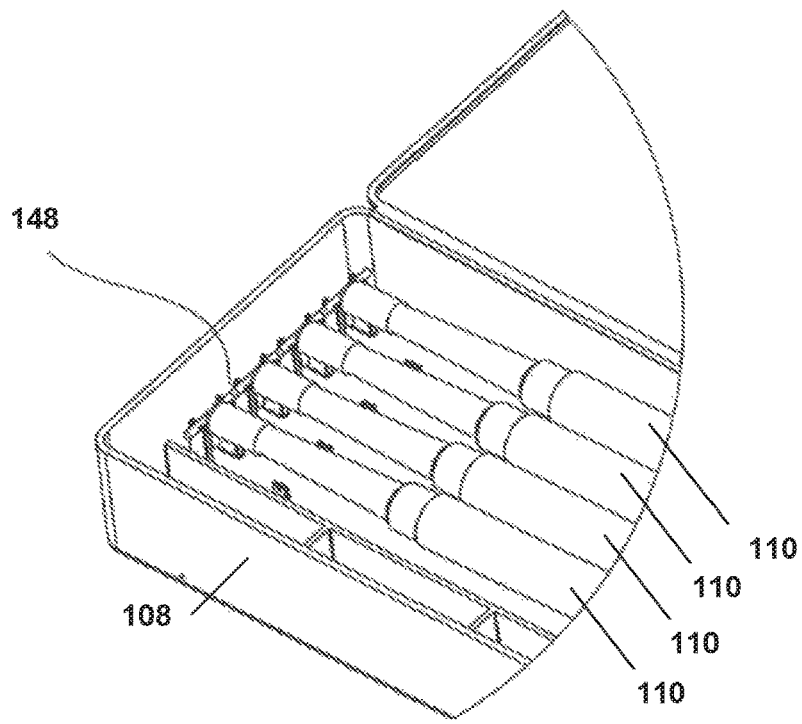
FIG. 12 depicts a close up view of a single hinge mechanism to control the position of all syringes within the box or pouch.

FIG. 12 depicts a close up view of a single hinge mechanism to control the position of all syringes 110 within the housing 108 (e.g., box or pouch) individually or collectively. As can be seen, the hinge mechanism rod 148 extends continuously and attaches to all syringe caps 138. The rod 148 can be one continuous rod, such that all syringes will rotate collectively. The rod 148 can also be segmented between syringe caps 138, allowing independent rotation. In particular embodiments, when segmented, the segments of the rod can be locked into a defined relationship, again providing collective rotation of all syringes.

Embodiments disclosed herein include methods of making and using the injection systems disclosed herein. A housing may be formed using any suitable materials. In some embodiments, one or more storage compartments may be formed in the housing. Medical supplies, such as an antiseptic wipe or a bandage, may be loaded into a storage compartment of an injection system (e.g., a storage compartment of a plunger, a storage compartment in the housing, and the like). An antiseptic wipe or sponge, for example, can be used to clean an injection site for administration of the primary medication. In some embodiments, methods include loading a primary medication into one or more syringes. In other embodiments, a primary medication is pre-loaded into a syringe. In particular embodiments, the syringe is detached from a syringe cap prior to use. In such embodiments, an outlet body and/or a connector may be attached to the distal end of the medication chamber prior to use. A first plunger can then be depressed in order to dispense the primary medication, which, in some embodiments, is pre-loaded in a first syringe. After use, the syringe can be placed back into the housing. In some embodiments, the syringe can be reattached to a syringe cap. In such embodiments, an outlet body and/or connector may be removed before the syringe is reattached to the syringe cap. In some embodiments, the syringe cap may cover an outlet body and/or connector.

Before or after administration of the primary medication, a supporting medication or a supplemental medication may be injected or otherwise administered. In embodiments where the supporting medication or the supplemental medication are in a formulation which is suitable for administration by a syringe (such as intramuscular injection, intravenous injection, intranasal administration, etc.), the supporting medication or the supplemental medication can be loaded into the syringe. In some embodiments, the supporting medication or supplemental medication may be loaded into one or more syringes by a user. In other embodiments, the supporting medication or the supplemental medication may be pre-loaded into one or more syringes.

In some embodiments, the supporting medication or the supplemental medication may be in a form suited for oral administration, such as a tablet or capsule, and may be loaded into a storage compartment of the injection system. For example, a capsule containing a supplemental medication formulated for oral administration can removed from a storage compartment and administered. In some embodiments, the supporting medication or the supplemental medication may be pre-loaded in a storage compartment of the injection system. In other embodiments, the supporting medication or the supplemental medication may be loaded into a storage compartment of the injection system by a user.

In embodiments disclosed herein, an injection system can be provided with instructions for use and/or storage. In some embodiments, the instructions can be in the form of written instructions (e.g., a set of numbered steps) and/or graphic representations (e.g., cartoons, line drawings, diagrams, and the like). In various embodiments, the instructions can be on paper and provided with the injection system; on a sticker or stickers attached to the injection system or attached to packaging associated with the injection system; printed on packaging associated with the injection system; or in any other way that would adequately provide the information to a user. In some embodiments, a web address or a code, such as a QR code, that directs the user to a webpage or application containing such instructions can be provided on or with the injection system, such as on paper and provided with the injection system; on a sticker or stickers attached to the injection system or attached to packaging associated with the injection system; or printed on packaging associated with the injection system. In such embodiments, instructional videos, animations, and the like may also be provided.

In particular embodiments, the instructions for use will direct replacement of medications and medical supplies based on shelf-life or expiration dates of medications and supplies that can be used with the embodiment. Instructions can also direct replacement of medications and medical supplies upon use. End users may subscribe to a medication or medical supply replacement service. In these embodiments, medications and/or medical supplies can be sent to the end user upon request and/or upon a schedule. Instructions can also request that end users provide feedback regarding experiences when using embodiments disclosed herein. The described instructions and request for feedback can be provided on paper, a CD-Rom, a website, or any other appropriate method of communication with end users.

In some embodiments, one or more visual indicators may be provided on or with the injection system disclosed herein, such as on paper and provided with the injection device system on a sticker or stickers attached to the injection system or attached to packaging associated with the injection system; or printed on packaging associated with the injection system. In such embodiments, the one or more visual indicators may indicate information that may be useful to a user, a medical provider, a medical facility, etc., such as the content of an injection system, the content of a syringe of an injection system, and/or the content of a storage compartment of an injection system. In embodiments, the one or more visual indicators may indicate dosage, expiration date, or any other information that may be useful to a user, a medical provider, a medical facility, and the like. In some embodiments, the one or more visual indicators can include codes, such as barcodes, QR codes, and the like. In such embodiments, the codes can be used by a user, a medical provider, a medical facility, and the like to track an injection system, to track the content of an injection system, to track the content of a syringe of an injection system, to track the content of a storage compartment of an injection system, and the like. A user, a medical provider, a medical facility, etc. may wish to track injection system and the contents therein for inventory purposes, for example. In further embodiments, the codes can be used to confirm the contents of an injection system, the contents of a syringe of an injection system, the content of a storage compartment of an injection system, and the like; or to update the listed contents of an injection system, a syringe of an injection system, the content of a storage compartment of an injection system, and the like, in a tracking system.

Particular embodiments of the injection systems disclosed herein are provided with therapeutically effective amounts of medications. More particular embodiments of the injection systems disclosed herein are provided with therapeutically effective amounts of medications to treat allergies, anaphylaxis, or heart conditions.

A therapeutically effective amount includes those that provide prophylactic treatments and/or therapeutic treatments.

A "prophylactic treatment" includes a treatment administered to a person or animal who does not yet display signs or symptoms of a medical condition but is expected to develop them or who displays only early signs or warning symptoms for the development of the medical condition such that treatment is administered for the purpose of diminishing, preventing, or decreasing the risk of the medical conditioning developing at all or developing further. Thus, a prophylactic treatment functions as a preventative treatment against medical conditions.

A "therapeutic treatment" includes treatments administered to a person or animal experiencing a medical condition for the purpose of reducing, controlling, or eliminating the negative effects of the medical condition.

One example of a medical condition that can be treated with the injection systems disclosed herein is allergic reaction. Allergic reactions, include allergic rhinitis, asthma, atopic dermatitis, food allergy, anaphylaxis, and shock. Anaphylaxis and shock are the most severe forms of allergic reaction and, if untreated, can result in death. All of these disorders are mediated, to some extent, by immediate hypersensitivity reactions in which the activation of inflammatory cells leads rapidly to the release of vasoactive mediators, such as histamine, platelet activating factor (PAF), cytokines, and proteolytic enzymes.

Symptoms of allergic reactions include abdominal pain; coughing; cramps; diarrhea; dizziness; eczema; fainting; hives; itching of the mouth, throat, and/or skin; lightheadedness; nasal congestion; nausea; rashes; throat closure; tingling of the mouth, throat, and/or skin; shortness of breath; swelling of the lips, tongue, and/or skin; trouble breathing; vomiting; weak pulse; and/or wheezing. Therapeutically effective amounts in relation to allergic reactions prevent, reduce, control, or eliminate one or more of these symptoms of an allergic reaction.

Exemplary medications that can be used to treat allergic reactions with the injection systems disclosed herein include antihistamines (e.g., ALLEGRA® (Aventisub II Inc., Greenville, Del.), ASTELIN® (Meda Pharmaceuticals Inc., Somerset, N.J.), BENADRYL® (Warner-Lambert Company LLC, Morris Plains, N.J.), CHLOR-TRIMETON® (MSD Consumer Care, Inc., Memphis, Tenn.), CLARINEX® (Merck Sharp & Dohme Corp., Whitehouse Station, N.J.), CLARITIN® (MSD Consumer Care, Inc., Memphis, Tenn.), DIMETANE® (Citron Pharma LLC, East Brunswick, N.J.), ELESTAT® (Boehringer Ingelheim International GMBH, Germany), pheniramine maleate (OCU-HIST™, Pfizer, Inc., New York, N.Y.), OPTIVAR® (Meda Pharmaceuticals Inc., Somerset, N.J.), PATANOL® (Alcon Research, Ltd., Fort Worth, Tx), TAVIST™, XYZAL™, ZYRTEC® (Johnson & Johnson Corp., New Brunswick, N.J.)); decongestants (e.g., AFRIN® (MSD Consumer Care, Inc., Memphis, Tenn.), SUDAFED® (Johnson & Johnson Corporation, New Brunswick, N.J.), NEO-SYNEPHRINE® (Foundation Consumer Healthcare, LLC, Dover, Del.); combination allergy medications (e.g., ALLEGRA-D® (Aventisub II Inc., Greenville, Del.), BENADRYL ALLERGY AND SINUS (Warner-Lambert Company LLC, Morris Plains, N.J.), CLARITIN-D® (MSD Consumer Care, Inc., Memphis, Tenn.), DYMISTA® (Meda Pharmaceuticals Inc., Somerset, N.J.), NAPHCON® (Alcon Research, Ltd., Fort Worth, Tex.), OPTIVAR® (Meda Pharmaceuticals Inc., Somerset, N.J.), PATANOL® (Alcon Research, Ltd. Fort Worth, Tex.), SEMPREX-D® (Actient Pharmaceuticals LLC, Chesterbrook, PN), TYLENOL ALLERGY AND SINUS® (Johnson & Johnson, New Brunswick, N.J.), VASOCON® (Novartis Ag, Basel Switzerland), ZADITOR® (Novartis Ag, Basel, Switzerland), ZYRTEC-D™); steroids (e.g., corticosteroids, ADVAIR® (Glaxo Group, Middlesex, UK), AEROBID® (Forest Laboratories, Inc., New York, N.Y.), ALREX® (Bausch & Lomb Inc., Rochester, N.Y.), ALVESCO® (Takeda GMBH, Germany), ASMANEX® (Merck Sharp & Dohme, Whitehouse Station, N.J.), AZMACORT® (Abbvie Respiratory LLC, Chicago, Ill.), BECONASE® (Glaxo Group, Middlesex, UK), DELTASONE® (Space Age Holdings LLC, Viejo, Calif.), Dexamethasone, FLONASE® (Glaxo Group, Middlesex, UK), FLOVENT® (Glaxo Group, Middlesex, UK), Fluticasone, NASOCORT™, NASONEX® (Merck Sharp & Dohme Corp., Whitehouse Station, N.J.), Prednisone, PULMICORT® (Astrazeneca AB, Sodertalje, Sweden), QNASL® (Teva Respiratory, LLC, Horsham, PN), beclomethasone dipropionate (Q-VAR® (Ivay, LLC, Horsham, Pa.)), RHINOCORT® (Astra Aktiebolag Corp., Sodertalje, Sweden), SYMBICORT® (Astrazeneca AB, Sodertalje, Sweden), VERAMYST® (Glaxo Group Middlesex, UK), ZETONNA® (Takeda GMBH Corporation, Germany)); bronchodilators (e.g., MAXAIR® (Medicis Pharmaceutical Corporation, Scottsdale, Ariz.), PROVENTIL® (Merck Sharp & Dohme Corp., Whitehouse Station, N.J.), PRO-AIR™, VENTOLIN® (Glaxo Group, Middlesex, UK), XOPENEX® (Sunovion Pharmaceuticals Inc., Marlborough, Mass.)); mast cell stabilizers (e.g., ALAMAST® (Santen Pharmaceutical Co., Ltd., Osaka, Japan), ALOCRIL® (Allergan, Inc., Irvine, Calif.), ALOMIDE® (Alcon Research, Ltd, Fort Worth, Tex.), CROLOM® (Bausch & Lomb Inc., Rochester, N.Y.), INTAL® (Fera Pharmaceuticals, LLC, Locust Valley, N.Y.), NASALCROM® (Pharmacia & Upjohn Co., Irvington, N.Y.), sodium cromoglicate (OPTICROM™ Adventis Pharma, Ltd., Surrey, UK), TILADE® (King Pharmaceuticals, Inc., Bristol, Tenn.)); leukotriene modifiers (e.g., ACCOLATE® (Par Pharmaceutical, Inc. Spring Valley, N.Y.) (zafirlukast), SINGULAIR® (Merck Sharp & Dohme Corp. Whitehouse Station, N.J.) (monteleukast), ZYFLO® (Chiesi Usa, Inc. Cary, N.C.) (zileuton)); and immunotherapy (e.g., allergy shots, GRASTEK® (Merck Sharp & Dohme Corp., Whitehouse Station, N.J.), ORALAIR® (Stallergenes SA, Antony, France), RAGWITEK® (Merck Sharp & Dohme Corp., Whitehouse Station, N.J.)). Medications described below in relation to anaphylaxis can also be used to treat allergies.

Anaphylaxis refers to a severe, potentially life-threatening systemic hypersensitivity reaction characterized by being rapid in onset with life-threatening airway, breathing, or circulatory problems. It is usually associated with skin and mucosal changes.

Clinical criteria for diagnosing anaphylaxis include presence of any one of the following three criteria: (1) acute onset of an illness (minutes to several hours) with involvement of the skin, mucosal tissue, or both and one or both of the following: (a) respiratory compromise; and (b) reduced blood pressure or associated symptoms of end-organ dysfunction (e.g., hypotonia, syncope, incontinence); (2) two or more of the following that occur rapidly after exposure to a likely allergen: (a) skin or mucosal tissue involvement (e.g., generalized hives, itch-flush, swollen lips, tongue, or uvula); (b) respiratory compromise; (c) reduced blood pressure or associated symptoms of end-organ dysfunction; and (d) persistent gastrointestinal symptoms (e.g., abdominal pain, vomiting); or (3) reduced blood pressure after exposure to a known allergen (minutes to several hours): (a) infants and children: low systolic blood pressure (age specific) or >30% decrease in systolic blood pressure or (b) adults: systolic blood pressure of <90 mmHg or >30% decrease from baseline. Therapeutically effective amounts in relation to anaphylactic reactions prevent, reduce, control, or eliminate one or more of these symptoms of an anaphylactic reaction.

Exemplary medications that can be used to treat anaphylactic reactions with the injection systems disclosed herein include adrenaline, short-acting beta-2 adrenergic agonists (in particular embodiments, inhaled), H1-H4-antihistamines (in particular embodiments, orally administered), corticosteroids, glucocorticosteroids (in particular embodiments, systemic or nebulized), and glucagon. Additional exemplary medications that can be used to treat anaphylactic reactions with the injection systems disclosed herein include H1 antihistamines (e.g., Acrivastine; Azelastine; Bilastine; Brompheniramine; Buclizine; Bromodiphenhydramine; Carbinoxamine; Cetirizine (ZYRTEC® (Johnson & Johnson Corp., New Brunswick, N.J.)); Chlorpromazine; Cyclizine; Chlorpheniramine; Chlorodiphenhydramine; Clemastine; Cyproheptadine; Desloratadine; Dexbrompheniramine; Dexchlorpheniramine; Dimenhydrinate; Dimetindene; Diphenhydramine (BENADRYL® (Warner-Lambert Company LLC, Morris Plains, N.J.); Doxylamine; Ebastine; Embramine; Fexofenadine (ALLEGRA® (Aventisub II Inc. Greenville, Del.)); Hydroxyzine (VISTARIL® (Pfizer, Inc., N.Y., NY)); Levocetirizine; Loratadine (CLARITIN® (MSD Consumer Care, Inc., Memphis, Tenn.); Meclozine; Mirtazapine; Olopatadine; Orphenadrine; Phenindamine; Pheniramine; Phenyltoloxamine, Promethazine; Pyrilamine; Quetiapine (SEROQUEL® (Astrazeneca UK, London, England)); Rupatadine; Tripelennamine; Triprolidine); H2 antihistamines (e.g., Cimetidine; Famotidine; Lafutidine; Nizatidine; Ranitidine; Roxatidine; Tiotidine); H3 antihistamines (e.g., Clobenpropit; ABT-239; Ciproxifan; Conessine; A-349,821; Thioperamide); H4 antihistamines (e.g., Thioperamide; JNJ 7777120; VUF-6002); atypical antihistamines (e.g., Catechin; Tritoqualine); and mast cell stabilizers (e.g., ALAMAST® (Santen Pharmaceutical Co., Osaka, Japan), ALOCRIL® (Allergan, Inc., Irvine, Calif.), ALOMIDE® (Alcon Research, Ltd., Fort Worth, Tex.), Cromoglicate (cromolyn; CROLOM® (BAUSCH & LOMB INC, Rochester, N.Y.)), INTAL® (Fera Pharmaceuticals, LLC, Locust Valley, N.Y.), NASALCROM® (Pharmacia & Upjohn Co, Irvington, N.H.), NEDOCROMIL™, OPTICROM™, TILADE® (King Pharmaceuticals, Inc, Bristol, Tenn.)).

The following exemplary medications (as well as others in the classes of compounds they represent) can additionally be provided as supporting, redundant, or supplemental medications to those described in the preceding paragraph: ACCOLATE® (Par Pharmaceutical, Inc. Spring Valley, N.Y.) (zafirlukast), ADVAIR® (Glaxo Group, Middlesex, UK), AFRIN® (MSD Consumer Care, Inc., Memphis, Tenn.), AEROBID® (Forest Laboratories, Inc., New York, N.Y.), ALLEGRA® (Aventisub II Inc., Greenville, Del.), ALREX® (Bausch & Lomb Inc., Rochester, N.Y.), ALVESCO® (Takeda GMBH, Germany), ASMANEX® (Merck Sharp & Dohme, Whitehouse Station, N.J.), ASTELIN® (Meda Pharmaceuticals Inc., Somerset, N.J.), AZMACORT® (Abbvie Respiratory LLC, Chicago, Ill.), BECONASE® (Glaxo Group, Middlesex, UK), BENADRYL ALLERGY AND SINUS™, CHLOR-TRIMETON® (MSD Consumer Care, Inc., Memphis, Tenn.), CLARINEX® (Merck Sharp & Dohme Corp., Whitehouse Station, N.J.), CLARITIN-D® (MSD Consumer Care, Inc., Memphis, Tenn.), DELTASONE® (Space Age Holdings LLC, Viejo, Calif.), Dexamethasone, DIMETANE® (Citron Pharma LLC, East Brunswick, N.J.), DYMISTA® (Meda Pharmaceuticals Inc., Somerset, N.J.), ELESTAT® (Boehringer Ingelheim International GMBH, Germany), FLONASE® (Glaxo Group, Middlesex, UK), FLOVENT® (Glaxo Group, Middlesex, UK), FLUTICASONE™, MAXAIR® (Medicis Pharmaceutical Corporation, Scottsdale, Ariz.), NAPHCON® (Alcon Research, Ltd., Fort Worth, Tex.), NASOCORT™, NASONEX® (Merck Sharp & Dohme Corp., Whitehouse Station, N.J.), NEO-SYNEPHRINE® (Foundation Consumer Healthcare, LLC, Dover, Del.), OCU-HIST™, OPTIVAR® (Meda Pharmaceuticals Inc., Somerset, N.J.), PATANOL® (Alcon Research, Ltd., Fort Worth, Tx), prednisone, PRO-AIR™, PROVENTIL® (Merck Sharp & Dohme Corp., Whitehouse Station, N.J.), PULMICORT® (Astrazeneca AB, Sodertalje, Sweden), QNASL® (Teva Respiratory, LLC, Horsham, PN), Q-VAR™, RHINOCORT® (Astra Aktiebolag Corp., Sodertalje, Sweden), SEMPREX-D® (Actient Pharmaceuticals LLC, Chesterbrook, PN), SINGULAIR® (Merck Sharp & Dohme Corp. Whitehouse Station, N.J.) (monteleukast), SUDAFED® (Johnson & Johnson Corporation, New Brunswick, N.J.),), SYMBICORT® (Astrazeneca AB, Sodertalje, Sweden), TAVIST™, TYLENOL ALLERGY AND SINUS® (Johnson & Johnson, New Brunswick, N.J.), VASOCON® (Novartis Ag, Basel Switzerland), VENTOLIN® (Glaxo Group, Middlesex, UK), VERAMYST® (Glaxo Group Middlesex, UK), XOPENEX® (Sunovion Pharmaceuticals Inc., Marlborough, Mass.), XYZAL™, ZADITOR® (Novartis Ag, Basel, Switzerland), ZYRTEC-D™, ZETONNA® (Takeda GMBH Corporation, Germany), and ZYFLO® (Chiesi Usa, Inc. Cary, N.C.) (zileuton).

Other examples of medical conditions that can be treated with the injection systems disclosed herein are heart conditions, such as arrhythmias, heart attacks or cardiac arrest. Symptoms of heart conditions include anxiety; chest discomfort; chest pressure or squeezing; dizziness; fatigue; lack of appetite; lightheadedness; loss of consciousness; nausea; pain (e.g., beginning in the chest and spreading to the shoulders, arms, elbows, back, neck, jaw, or abdomen); persistent coughing or wheezing; rapid or irregular pulse; shortness of breath; sweating (e.g., cold sweat); swelling (often in the feet, ankles, legs, or abdomen); vomiting; and/or weakness.

Therapeutically effective amounts in relation to heart conditions, such as heart attacks or cardiac arrest, prevent, reduce, control, or eliminate one or more of these symptoms of a heart condition, addressing the underlying condition leading to the symptom, and/or can preserve heart muscle function following occurrence of the condition.

Exemplary medications that can be used to treat heart conditions with the injection systems disclosed herein include angiotensin-converting enzyme (ACE) inhibitors (e.g., Benazepril (LOTENSIN® (Novartis Pharmaceuticals Corporation, East Hanover, N.J.), Captopril (CAPOTEN® (Phar Pharmaceutical, Inc., Woodcliff Lake, N.J.)), Enalapril (VASOTEC® (Biovail Laboratories Intl., Christ Church, Barbados)), Fosinopril (MONOPRIL® (E. R. Squibb & Sons, L.L.C., Princeton, N.J.)), Lisinopril (PRINIVIL® (Merck Sharp & Dohme Corp., Whitehouse Station, N.J.), ZESTRIL® (Alvogen Pharma US, INC., Pine Brook, N.J.)), Moexipril (UNIVASC® (UCB Mfg., Inc., Rochester, N.Y.)), Perindopril (ACEON® (Biofarma Societe Par Actions Simplifiee, France)), Quinapril (ACCUPRIL® (Warner-Lambert Company, Morris Plains, N.J.)), Ramipril (ALTACE® (King Pharmaceuticals Research And Development, Inc., Cary, N.C.)), Trandolapril (MAVIK® (Abbvie Deutschland Gmbh & Co., Germany)); angiotensin II receptor antagonists (e.g., Candesartan (ATACAND® (AstraZeneca AB, Sodertalje, Sweden)), Eprosartan (TEVETEN® (Abbvie Respiratory LLC, Chicago, Ill.)), Irbesartan (AVAPRO® (Sanofi Societe Anonyme, Paris, France)), Losartan (COZAAR® (Merck Sharp & Dohme Corp., Whitehouse Station, N.J.)), Telmisartan (MICARDIS® (Boehringer Ingelheim KG, Germany)) and Valsartan (DIOVAN® (Novartis Corporation, Summit, N.J.))); anti-arrhythmics (e.g., BETAPACE® (Bayer Pharma Aktiengesellschaft, Germany) (SOTALOL™), CORDARONE® (Sanofi Societe Anonyme, Paris, France) (Amiodarone), Lidocaine, PROCANBID® (Parkedale Pharmaceuticals, Inc., Rochester, Mich.) (Procainamide), TAMBOCOR® (Medicis Pharmaceutical Corp., Scottsdale, Ariz.) (Flecainide)); Anti-coagulants (e.g., Dalteparin (FRAGMIN® (Pfizer Health AB, Stockholm, Sweden)), Danaparoid (ORGARAN® (Aspen Global Incorporated, Grand Bay, Mauritius)), Enoxaparin (LOVENOX® (Aventis Pharma S.A., Antony, France)), Heparin (various), Tinzaparin (INNOHEP® (Leo Pharmaceutical Products Ltd., Ballerup, Denmark), Warfarin (COUMADIN® (Bristol-Myers Squibb Pharma Company, Wilmington, Del.))); Anti-hypotensive/vasopressors (e.g., Sympathomimetics (e.g., Amezinium, Dopamine, Dobutamine, Ephedrine hydrochloride, Epinephrine, Midodrine, Noradrenaline hydrotartrate, Phenylephrine (Mesaton)); Myotropic medications; Angiotensinamide, S-alkylisothiouronium derivatives (e.g., Difetur, Izoturon); Glucocorticoids and mineralocorticoids (e.g., Betamethasone, Dexamethasone, Fludrocortisone, Hydrocortisone, Prednisolone, Prednisone); Analeptics (e.g., Bemegride, Caffeine, Camphora, Cordiamine); Psychotropics (e.g., Amphetamine, Atomoxetine, Bupropion, Duloxetine, Methamphetamine, Methylphenidate, Reboxetine, Venlafaxine); Positive inotropic agents (e.g., Amrinone, Cardiac glycosides (e.g., Corglycon, Digoxin, Strophantin K), Milrinone); anti-platelet agents (e.g., Aspirin, Clopidogrel (PLAVIX® (Sanofi Societe Anonyme, Paris, France)), Dipyridamole, Ticlopidine); beta blockers (e.g., Acebutolol (SECTRAL® (Aventis Pharma S.A., Cedex, France)), Atenolol (TENORMIN® (Alvogen Pharma US, Inc., Pine Brook, N.J.)), Betaxolol (KERLONE® (Sanofi Societe Anonyme, Paris, France)), Bisoprolol/hydrochlorothiazide (ZIAC® (Teva Women's Health, Inc., Woodcliff Lake, N.J.)), Bisoprolol (ZEBETA® (Teva Women's Health, Inc., Woodcliff Lake, N.J.)), Carteolol (CARTROL® (Abbvie Inc., Chicago, Ill.), Metoprolol (LOPRESSOR® (Novartis Pharmaceuticals Corp., East Hanover, N.J.), TOPROL XL® (Astrazeneca LP, Wayne, PN)), Nadolol (CORGARD® (King Pharmaceuticals Research And Development, Inc., Bristol, Tenn.)), Propranolol (INDERAL® (WYETH LLC, London, UK), Sotalol (BETAPACE® (Bayer Pharma, Berlin, Germany), Timolol (BLOCADREN® (Merck Sharp & Dohme CORP, Whitehouse Station, N.J.))); calcium channel blockers (e.g., Amlodipine (NORVASC® (Pfizer, Inc., New York, N.Y.), LOTREL® (Novartis Corp., Summit, N.J.)), Bepridil (VASCOR® (Johnson & Johnson, Corp., New Brunswick, N.J.)), Diltiazem (CARDIZEM® (Valeant Intl., Bermuda), TIAZAC® (Biovail Laboratories Intl., Christ Church, Barbados)), Felodipine (PLENDIL® (Astrazeneca AB, Sodertalje Sweden), Nifedipine (ADALAT® (Bayer Aktiengesellschaft, Germany), PROCARDIA® (Pfizer, Inc., New York, N.Y.)), Nimodipine (NIMOTOP® (Bayer Aktiengesellschaft, Germany)), Nisoldipine (SULAR® (Shionogi Inc., London, UK), Verapamil (CALAN® (G. D. SEARLE & CO., Skokie, Ill.), ISOPTIN® (FSC Laboratories, Inc., Charlotte, N.C.), VERELAN® (Elan Pharma Intl., Westmeath, Ireland)); cholesterol-lowering medications (e.g., Clofibrate, Gemfibrozil, nicotinic acid (niacin), Resins, Statins); diuretics (e.g., Amiloride (MIDAMOR® (Paddock Laboratories, Inc., Minneapolis, Minn.)), Bumetanide (BUMEX® (Validus Pharmaceuticals LLC, Parsippany, N.J.)), Chlorothiazide (DIURIL® (Merck Sharp & Dohme Corp., Whitehouse Station, N.J.)), Chlorthalidone (HYGROTON® (Amneal Pharmaceuticals LLC, Bridgewater, N.J.)), Furosemide (LASIX® (Sanofi-Aventis Deutschland, Frankfurt, Germany), Hydro-chlorothiazide (ESIDRIX® (Ciba-Geigy Corp., Summit, N.J.), HYDRODIURIL™), Indapamide (LOZOL® (Biofarma Corporation, France) and Spironolactone (ALDACTONE® (Pharmacia & Upjohn Company LLC, Kalamazoo, Mich.)); Nitroglycerin; pH elevators (e.g., sodium bicarbonate); and Thrombolytics (e.g., Reteplase, Lanoteplase, tissue plasminogen activator, Staphylokinase, Streptokinase (SK), Tenecteplase, Urokinase).

In various embodiments, dosage can be customized for the subject. In such embodiments, dietary factors, cardiovascular function, gastrointestinal function, liver function, immunologic function, renal function, age, sex, body weight, and the like may be considered. Examples of therapeutically effective amounts to treat conditions can include 0.1 to 5 µg/kg or from 0.5 to 1 µg/kg body weight of a person or animal. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

In summary, disclosed herein is an injection system that includes (i) an injection device with a medication chamber; and (ii) a storage compartment. The storage compartment can be within the injection device itself or can be independent of the injection device provided elsewhere within the injection system. The disclosed systems allow a user to easily access and use the curated contents in accordance with standard medical practices. Together, the medication chamber and storage compartment provide: primary medications (e.g., epinephrine to treat an allergic reaction); supporting medications (e.g., an antiseptic to treat the site of administration); redundant doses (e.g., a second dose of epinephrine should the first dose be insufficient); supplemental medications (e.g., a dose of an antihistamine or steroid); and/or medications and materials to support administration of the medications (e.g., one or more medications with needles, sterilizing materials, gauzes, and/or bandages).

Exemplary Embodiments

1. A medical device including a housing, at least two syringes associated with a hinge mechanism, a storage compartment, and a primary medication.
2. A medical device of embodiment 1, further including a supporting medication, a redundant dose of the primary medication, or a supplemental medication.
3. A medical device of any one of embodiments 1 or 2, further including a medical supply.
4. A medical device of any one of embodiments 1-3, wherein the hinge mechanism is biased to move the at least two syringes into an in-use position.
5. A medical device of any one of embodiments 1-4, wherein the storage compartment is integrated into the housing.
6. A medical device of any one of embodiments 1-5, wherein the storage compartment houses a supporting medication, a redundant dose, or a supplemental medication to a primary medication.
7. A medical device of any one of embodiments 1-6, wherein the storage compartment houses a medical supply.
8. A medical device of any one of embodiments 1-7, wherein the medical supply includes a sponge.
9. A medical device of any one of embodiments 1-8, wherein the storage compartment includes an opening covered by a removable seal.
10. A medical device of any one of embodiments 1-9, wherein the removable seal is a cap, foil, or wrap.
11. A medical device of any one of embodiments 1-10, wherein a plunger of one syringe of the at least two syringes includes a second storage compartment.
12. A medical device of any one of embodiments 1-11, wherein a sponge extends outside of the second storage compartment after a seal is removed from an opening on the second storage compartment.
13. A medical device of any one of embodiments 1-12, wherein the hinge mechanism allows independent movement each syringe of the at least two syringes from a storage position to an in-use position.
14. A medical device of any one of embodiments 1-13, wherein the primary medication is provided in a therapeutically effective amount to treat an allergic reaction or a heart condition.
15. A medical device including:
    a housing;
    two or more syringes arranged substantially parallel to each other, each syringe having a distal end through which a medication can be expelled and a proximal end through which a plunger can be inserted; and
    two or more caps into which the distal end of a syringe of the two or more syringes is releasably inserted, wherein the two or more caps are attached to the housing via a hinge, thereby enabling the two or more caps to rotate about an axis via the hinge.
16. A medical device of embodiment 15, wherein a first syringe of the two or more syringes houses a primary medication.
17. A medical device of any one of embodiments 15 or 16, wherein a second syringe of the two or more syringes houses a supporting medication, a redundant dose of the primary medication, or a supplemental medication.
18. A medical device of any one of embodiments 15-17, wherein the two or more caps are releasably attached to the housing via the hinge.
19. A medical device of any one of embodiments 15-18, further including a storage compartment.
20. A medical device of any one of embodiments 15-19, wherein the storage compartment houses a supporting medication, a redundant dose of the primary medication, or a supplemental medication.
21. A medical device of any one of embodiments 15-20, wherein the storage compartment houses medical supplies.
22. A medical device of any one of embodiments 15-21, wherein the medical supplies include a sponge.
23. A medical device of any one of embodiments 15-22, wherein the storage compartment includes an opening covered by a removable seal.
24. A medical device of any one of embodiments 15-23, wherein the removable seal is a cap, foil, or wrap.
25. A medical device of any one of embodiments 15-24, wherein one syringe of the two or more syringes houses a medication selected from epinephrine, an antihistamine, a corticosteroid, an anti-arrhythmic, a vasopressor, and a pH elevator.
26. A medical device of any one of embodiments 15-25, wherein the medical device is pre-loaded to treat an allergic reaction or a heart condition.
27. A medical device of any one of embodiments 15-26, including epinephrine, an antihistamine, a corticosteroid, an anti-arrhythmic, a vasopressor, a pH elevator, and/or an antiseptic.
28. A method including:
    obtaining a device including a housing, two or more syringes arranged substantially parallel to each other, each syringe having a distal end through which a medication can be expelled and a proximal end through which a plunger can be inserted, and two or more caps into which the distal end of a syringe is releasably inserted, wherein the two or more caps are attached to the housing via a hinge, thereby enabling the two or more caps to rotate about an axis via the hinge;

detaching a first syringe of the two or more syringes from a first cap of the two or more caps; and administering a primary medication housed in the first syringe to a subject.

29. The method of embodiment 28, wherein the device further includes a storage compartment, the storage compartment containing a medical supply, a supporting medication, or a supplemental medication.

30. The method of any one of embodiments 28 or 29, wherein the medical supply is an antiseptic wipe, and the method further includes:

removing the antiseptic wipe from the storage compartment, and cleaning an injection site of the subject prior to administering the primary medication.

31. The method of any one of embodiments 28-30, further including:

removing the supplemental medication from the storage compartment, and administering the supplemental medication to the subject.

32. The method of any one of embodiments 28-31, further including:

removing the supporting medication from the storage compartment, and administering the supporting medication to the subject.

33. The method of any one of embodiments 28-32, further including:

detaching a second syringe of the two or more syringes from a second cap of the two or more caps, and administering a content of the second syringe to the subject.

34. The method of any one of embodiments 28-33, wherein the content of the second syringe is a redundant dose of the primary medication, a supporting medication, or a supplemental medication.

35. A method including:

obtaining a device including a housing, at least two syringes associated with a hinge mechanism, a storage compartment, and a primary medication, wherein the primary medication is housed in a first syringe of the at least two syringes;

disassociating the first syringe from the hinge mechanism; and administering the primary medication to a subject via injection.

36. The method of embodiment 35, wherein the storage compartment contains a medical supply, a supporting medication, or a supplemental medication.

37. The method of any one of embodiments 35 or 36, wherein the medical supply is an antiseptic wipe, and the method further includes:

removing the antiseptic wipe from the storage compartment, and cleaning an injection site of the subject prior to administering the primary medication.

38. The method of any one of embodiments 35-37, further including:

removing the supplemental medication from the storage compartment, and administering the supplemental medication to the subject.

39. The method of any one of embodiments 35-38, further including:

removing the supporting medication from the storage compartment, and administering the supporting medication to the subject.

40. The method of any one of embodiments 35-39, further including:

disassociating a second syringe of the at least two syringes from the hinge mechanism, and administering a content of the second syringe to the subject.

41. The method of any one of embodiments 35-40, wherein the content of the second syringe is a redundant dose of the primary medication, a supporting medication, or a supplemental medication.

42. A method of making a medical device, the method including:

producing a housing, the housing associated with a hinge mechanism;

attaching a first cap and a second cap to the hinge mechanism, wherein the first cap and the second cap are enabled to rotate about an axis via the hinge mechanism; and releasably inserting a first distal end of a first syringe into the first cap and a second distal end of a second syringe in to the second cap such that the first syringe and the second syringe are substantially parallel to each other.

43. A method of embodiment 42, further including loading a primary medication into the first syringe.

44. A method of any one of embodiments 42 or 43, further including loading a redundant dose of the primary medication into the second syringe.

45. A method of any one of embodiments 42-44, further including loading a supporting medication or a supplemental medication into the second syringe.

46. A method of any one of embodiments 42-45, wherein the housing further includes a storage compartment, and wherein the method further includes:

inserting a medical supply, a supporting medication, or a supplemental medication into the storage compartment; and covering the storage compartment with the removable seal.

As will be understood by one of ordinary skill in the art, each embodiment disclosed herein can comprise, consist essentially of, or consist of its particular stated element, step, ingredient, or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. As used herein, a material effect would cause a statistically-significant reduction in the ability of a storage compartment to house medication or a medical supply.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, if references have been made to patents, printed publications, journal articles, and other written text throughout this specification (referenced materials herein), each of the referenced materials are individually incorporated herein by reference in their entirety for their referenced teaching.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising:
   a housing,
   at least two syringes, each syringe having a respective cap releasably attached thereto,
   a storage compartment in the housing, and
   a primary medication,
   wherein each cap is releasably attached to the housing via a hinge mechanism.

2. A medical device of claim 1, further comprising one or more of a supporting medication, a redundant dose of the primary medication, a supplemental medication and a medical supply.

3. A medical device of claim 1, wherein the hinge mechanism is biased to move the at least two syringes into an in-use position.

4. A medical device of claim 1, wherein the storage compartment is integrated into the housing.

5. A medical device of claim 1, wherein the storage compartment houses one or more of a supporting medication, a redundant dose, a supplemental medication to a primary medication and a medical supply.

6. A medical device of claim 1, wherein the storage compartment comprises an opening covered by a removable seal.

7. A medical device of claim 1, wherein a plunger of one syringe of the at least two syringes includes a second storage compartment.

8. A medical device of claim 1, wherein the hinge mechanism allows independent movement of each syringe of the at least two syringes from a storage position to an in-use position.

9. A medical device comprising:
a housing;
two or more syringes arranged substantially parallel to each other, each syringe having a distal end through which a medication can be expelled and a proximal end through which a plunger can be inserted; and
two or more caps into which the distal end of a syringe of the two or more syringes is releasably inserted, wherein at least one of the two or more caps is releasably attached to the housing via a hinge, thereby enabling the two or more caps to rotate about an axis via the hinge.

10. A medical device of claim 9, wherein a first syringe of the two or more syringes houses a primary medication.

11. A medical device of claim 10, wherein a second syringe of the two or more syringes houses one of a supporting medication, a redundant dose of the primary medication, and a supplemental medication.

12. A medical device of claim 9, further comprising a storage compartment.

13. A medical device of claim 12, wherein the storage compartment houses one or more of a supporting medication, a redundant dose of the primary medication, a supplemental medication and a medical supply.

14. A medical device of claim 12, wherein the storage compartment comprises an opening covered by a removable seal.

15. A method comprising:
obtaining a device comprising a housing, two or more syringes arranged substantially parallel to each other, each syringe having a distal end through which a medication can be expelled and a proximal end through which a plunger can be inserted, and two or more caps into which the distal end of a syringe is releasably inserted, wherein at least one of the two or more caps is releasably attached to the housing via a hinge, thereby enabling the two or more caps to rotate about an axis via the hinge;
detaching a first syringe of the two or more syringes from a first cap of the two or more caps; and
administering a primary medication housed in the first syringe to a subject.

16. The method of claim 15, wherein the device further comprises a storage compartment, the storage compartment containing one of a medical supply, a supporting medication, and a supplemental medication.

17. The method of claim 16, wherein the medical supply is an antiseptic wipe, and the method further comprises:
removing the antiseptic wipe from the storage compartment, and
cleaning an injection site of the subject prior to administering the primary medication.

18. The method of claim 16, further comprising:
removing the supplemental medication or the supporting medication from the storage compartment, and
administering the supplemental medication or the supporting medication to the subject.

19. The method of claim 15, further comprising:
detaching a second syringe of the two or more syringes from a second cap of the two or more caps, and
administering a content of the second syringe to the subject.

* * * * *